(12) United States Patent
Citterio et al.

(10) Patent No.: US 8,766,003 B2
(45) Date of Patent: Jul. 1, 2014

(54) PROCESS FOR THE IODINATION OF PHENOLIC DERIVATIVES

(75) Inventors: Attilio Citterio, Milan (IT); Elisa Battistini, Valperga (IT); Davide Belnome, Serra Riccò (IT); Federica Buonsanti, Turin (IT); Luciano Lattuada, Bussero (IT); Gabriella Leonardi, Milan (IT); Fulvio Uggeri, Codogno (IT); Evelin Vignale, Isola d'Asti (IT); Massimo Visigalli, Settala (IT)

(73) Assignee: Bracco Imaging S.p.A., Milan (IT)

( * ) Notice: Subject to any disclaimer, the term of this patent is extended or adjusted under 35 U.S.C. 154(b) by 34 days.

(21) Appl. No.: 13/702,223

(22) PCT Filed: Jun. 9, 2011

(86) PCT No.: PCT/EP2011/059594
§ 371 (c)(1),
(2), (4) Date: Dec. 5, 2012

(87) PCT Pub. No.: WO2011/154500
PCT Pub. Date: Dec. 15, 2011

(65) Prior Publication Data
US 2013/0072719 A1 Mar. 21, 2013

(30) Foreign Application Priority Data
Jun. 10, 2010 (EP) ..................................... 10165485

(51) Int. Cl.
C07C 231/12 (2006.01)
C07C 231/14 (2006.01)
C07B 39/00 (2006.01)

(52) U.S. Cl.
USPC ......................................... 564/156; 564/153

(58) Field of Classification Search
CPC ...... C07C 231/12; C07C 231/14; C07B 39/00
USPC .................................................. 564/153, 156
See application file for complete search history.

(56) References Cited

U.S. PATENT DOCUMENTS

| 4,739,100 A | 4/1988 | Adrian et al. |
| 5,856,596 A | 1/1999 | Nukada |

FOREIGN PATENT DOCUMENTS

| EP | 2199271 A1 | 6/2010 |
| EP | 1777215 B1 | 11/2010 |
| JP | S61-260041 A | 11/1986 |
| JP | H07-233106 A | 9/1995 |
| JP | 2002-531432 A | 9/2002 |
| JP | 2005-139079 A | 6/2005 |
| WO | 00/32561 A1 | 6/2000 |
| WO | 2006/016510 A1 | 2/2006 |
| WO | 2009/028608 A1 | 5/2009 |
| WO | 2009/103666 A2 | 8/2009 |

OTHER PUBLICATIONS

Patil, Bhagwan R. et al., Iodine and iodic acid: an efficient reagent combination for iodination of aryl hydroxy ketones, Tetrahedron Letters, vol. 46, Sep. 6, 2005, pp. 7179-7181, XP002607744, Elsevier, Amsterdam, NL, ISSN: 0040-4039.
PCT international Search Report for PCT/EP2011/059594, mail date Jul. 11, 2011.
PCT Written Opinion for PCT/EP2011/059594, mail date Jul. 11, 2011.
Kretzer, H., "Notes on iodosobenzoic acids [as translated from Zur Kenntniss der Jodosobenzoesauren]", Chemische Berichte, 1897, vol. 30, No. 2, pp. 1943-1948.
Lutjens, Jacob, "The chemical behaviour and the oxidation of tetraiodoterephthalic acid, and triiododiamidobenzoic acid [as translated from Ueber das chemische Verhalten und die Oxydation der Tetrajodterephtalsaure, und uber Trijoddiamidobenzoesaure]", Chemische Berichte, 1896, vol. 29, No. 3, pp. 2833-2839, No. 533.
Office Action for Japanese application No. 2013-513700, mail date—Apr. 15, 2014 (English translation).

*Primary Examiner* — Shailendra Kumar
(74) *Attorney, Agent, or Firm* — M. Caragh Noone

(57) ABSTRACT

The present invention relates to a process for the preparation of iodinated phenols; in particular; it relates to a process including the direct iodination, with suitably activated iodine, of 3,5-disubstituted phenol compounds to the corresponding 3,5-disubstituted-2,4,6-triiodophenols, which are useful intermediates for the synthesis of x-ray contrast media, and to the preparation of the contrast media themselves.

15 Claims, 5 Drawing Sheets

PROCESS FOR THE IODINATION OF PHENOLIC DERIVATIVES

CROSS-REFERENCE TO RELATED APPLICATIONS

This application is the national stage application of corresponding international application number PCT/EP2011/059594 filed Jun. 9, 2011, which claims priority to and the benefit of European application no. EP10165485.3, filed Jun. 10, 2010, all of which are hereby incorporated by reference in their entirety.

FIELD OF THE INVENTION

The present invention relates to a process for the preparation of triiodinated aromatic compounds. In particular, it relates to a process for the triiodination, with activated molecular iodine, of 3,5-disubstituted phenols to the corresponding 3,5-disubstituted-2,4,6-triiodophenols, which are useful intermediates for the synthesis of x-ray contrast agents, and to a general process for the preparation of the contrast agents themselves.

STATE OF THE ART

Iodinated contrast media are well-known compounds widely used in x-ray imaging diagnostic techniques. Suitable examples of the said compounds are, for instance, provided in WO2009/103666 (Bracco) and cited literature.

As a common feature, the chemical structure of the wide majority of them comprises a triiodinated aromatic nucleus which provides the enhanced contrast effect. Therefore, although carried out with a variety of routes, the preparation of these contrast agents includes, as a necessary step, the iodination of an aromatic substrate, mainly 5-aminoisophthalic groups, which undergo triiodination on the available 2, 4 and 6 positions, thus leading to the corresponding 3,5-disubstituted-2,4,6-triiodoaniline derivatives which are then converted and processed to the final agent, for instance as disclosed in U.S. Pat. No. 5,075,502.

The poly-iodination of suitable 3,5-disubstituted phenols may, alternatively, be exploited, leading to the corresponding 3,5-disubstituted-2,4,6-triiodophenols that may be then converted and processed to the expected final agent through the so-called Smile's rearrangement.

For a general reference to the above synthetic route and Smile's rearrangement see, for instance, WO 88/09328, WO 97/05097 and WO 00/32561 (Bracco).

The iodination reaction may be carried out according to different procedures known in the art. To this extent, in industrial processes currently used for preparing radiographic contrast agents, the iodination of the aromatic substrate is typically carried out by using solutions of iodine chloride (ICl) in concentrated hydrochloric acid (HCl) at high temperature or, alternatively, by means of analogous iodinating agents such as, for instance, $KICl_2$ or $NaICl_2$ in aqueous solution; see, for a general reference, U.S. Pat. No. 3,914,294 (Squibb), WO 92/14695 (Guerbet), U.S. Pat. No. 5,013,865 (Mallinckrodt), WO 96/37458 and WO 96/37459 (Fructamine).

The above methods suffer from major drawbacks due to the extremely acidic working conditions, that become increasingly harder due to HCl produced during the reaction, the corrosive properties of the iodinating agents and to their limited storage life.

As an example, Iomeprol, a well known radiographic contrast agent widely used in daily diagnostic practice, can be prepared by iodinating the key intermediate of formula

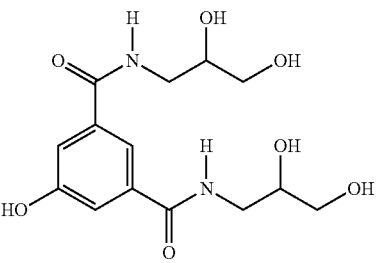 [SMILES: O=C(NCC(O)CO)c1cc(O)cc(C(=O)NCC(O)CO)c1]

to give the corresponding iodinated derivative of formula

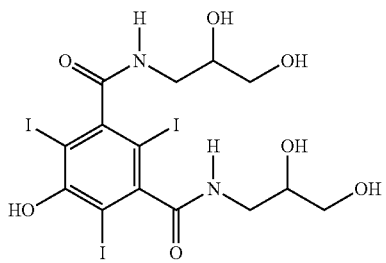 [SMILES: O=C(NCC(O)CO)c1c(I)c(O)c(I)c(C(=O)NCC(O)CO)c1I]

The iodination is generally carried out by using an aqueous solution of $KICl_2$ or $NaICl_2$ as iodinating agent, by keeping the reaction medium to pH around 9.5 with a suitable base, typically NaOH, for instance as disclosed in EP 185130.

Alternatively, the iodination of the phenolic substrate is carried out by using a solution of ICl as iodinating agent (composition: 44.5% I and 14% HCl w/w in $H_2O$), in an aqueous medium kept to a pH value from 6 to 7 by addition of a base, preferably NaOH, and to a temperature of 25° C., for instance as disclosed in WO00/32561.

To this extent it is clear that, when working on industrial scale, major problems arise from the need to handle, and, more importantly, to neutralize the extreme acidity of the iodinating reagent used. To this end, in fact, very large amounts of NaOH are required to neutralize either the HCl present in the iodinating solution or the HCl produced during the reaction.

Moreover, as the neutralization of such strong acid is extremely exothermic, the need to keep the reaction temperature around 25° C. forces to use long addition time, necessary to prevent a sudden as uncontrollable temperature increases, despite the iodination reaction is almost instantaneous.

Attempts have been, thus, addressed to iodination procedures alternative to the use of iodine chloride or derivatives thereof. In this context the electrochemical iodination processes of suitable aromatic substrates, for instance as disclosed in WO 96/37461, U.S. Pat. No. 3,833,490 and WO2009/103666 should be acknowledged.

The mono-iodination of ortho-hydroxy substituted aromatic carbonyl compounds with molecular iodine suitably activated by use of a strong oxidizing agent, including iodic acid, has been alternatively proposed by Patil et al. in *Tetrahedron Letters* 2005, 46, 7179-7181. The possibility of using the same iodinating system to further provide ortho/para diiodinated ortho-hydroxy aromatic carbonyl derivatives is suggested by the same authors in *ARKIVOC* 2006, 104-408. In both articles, commercial 95% aqueous ethanol was used as reaction solvent.

Furthermore, ES 528109 discloses the preparation of 2,4,6-triiodophenols with iodine activated by $H_2O_2$ (30%), in methanol, acidified with $H_2SO_4$ and heated to 60° C., with a referred yield of 44%.

SUMMARY OF THE INVENTION

The present invention provides a process for the tri-iodination of 3,5-disubstituted phenols or a salt thereof, that is carried out in an aqueous medium with molecular iodine suitably activated by the presence of an oxidizing agent, typically iodic acid, and an improved method for the preparation of x-ray contrast agents including the above iodination step.

DETAILED DESCRIPTION OF THE INVENTION

Figure 1:
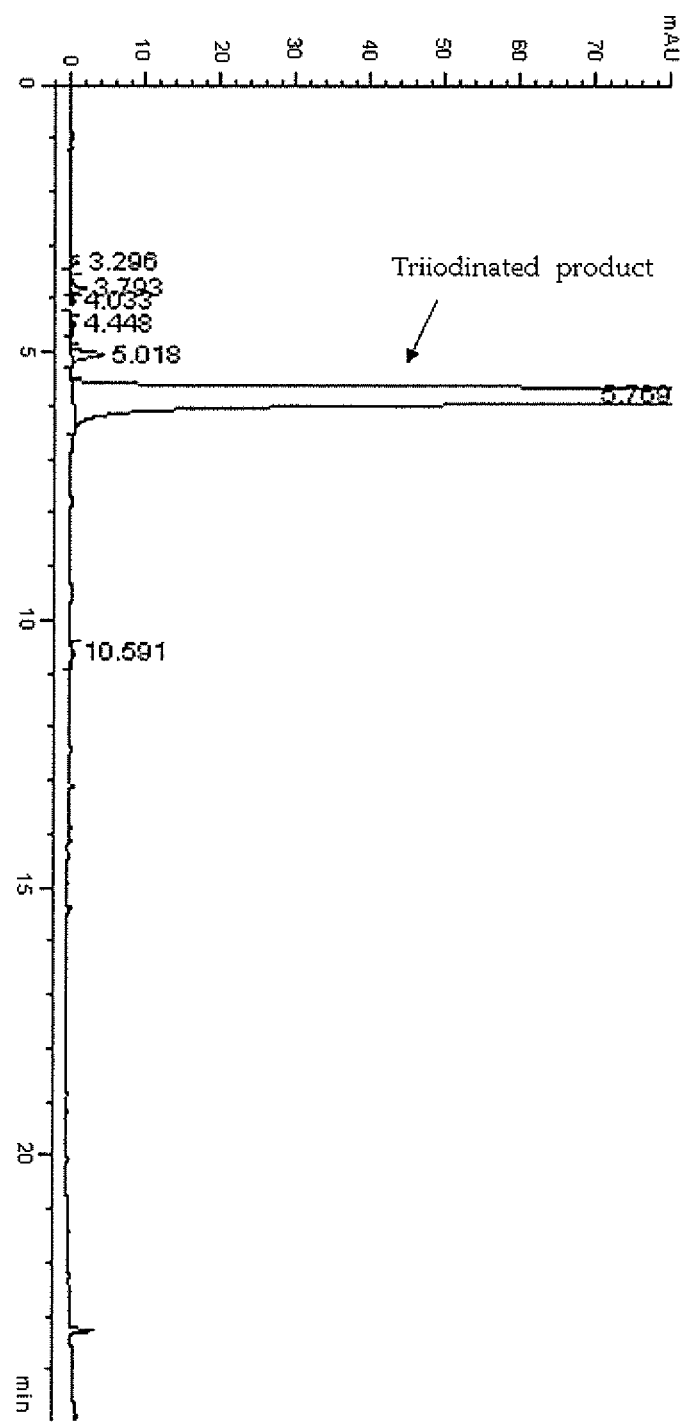
FIG. 1: Example 1: HPLC of the crude solution after 6 hours of reaction (final solution).

A first object of the present invention is a process for the preparation of triiodophenol compounds of formula 2,

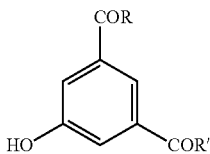

2 said process comprises iodinating a 3,5-disubstituted phenol of formula 1, or a salt thereof, with molecular iodine in the presence of iodic acid,

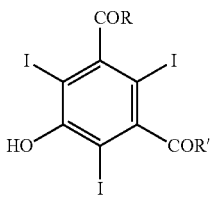

1 wherein:
R and R' represent, the same or different from each other, a group of formula $-NHR_1$ or of formula $-NR_2R_3$, wherein each $R_1$, $R_2$ and $R_3$ is, independently from each other, a straight or branched $C_1$-$C_6$ alkyl group which is optionally substituted by one or more groups selected from hydroxyl (—OH), $C_1$-$C_5$ alkoxy or hydroxyalkoxy groups.

The iodination process of the instant invention is conveniently carried out in an aqueous medium.

In the present description, unless otherwise provided, with the term straight or branched $C_1$-$C_6$ alkyl group we intend a linear or branched alkyl chain with from 1 to 6 carbon atoms. Suitable examples for alkyl groups comprise methyl, ethyl, n-propyl, isopropyl, n-butyl, isobutyl, see-butyl, tert-butyl, n-pentyl, n-hexyl, and the like.

The above alkyl groups may be further substituted by one or more hydroxyl, alkoxy or hydroxyalkoxy groups, as set forth above.

With the term $C_1$-$C_5$ alkoxy we intend any alkyl-oxy group wherein the alkyl moiety represents any of the above straight or branched alkyl group.

With hydroxyalkoxy group we intend any of the above $C_1$-$C_5$ alkoxy groups wherein the alkyl moiety is further substituted by one or more hydroxyl group.

Suitable examples of alkoxy or hydroxyalkoxy groups of the invention comprise, for instance, methoxy, ethoxy, n-propoxy, isopropoxy, n-pentoxy, 2-hydroxyethoxy, 2,3-dihydroxypropoxy, 1,3-dihydroxyisopropoxy, and the like.

According to a preferred embodiment of the process of the invention, within the compounds of formulae 1 and 2, R and R' represent, the same or different from each other, a group selected from $-NHR_1$ or $-NR_2R_3$ wherein each $R_1$, $R_2$ and $R_3$ is, independently from each other, a straight or branched $C_1$-$C_4$ alkyl group optionally substituted by from one to three hydroxyl groups such as, for instance, 1,3-dihydroxyisopropyl, 2,3-dihydroxypropyl, 1,3-dihydroxy-2-methyl-isopropyl, or 2,3,4-trihydroxybutyl.

Even more preferably, within the compounds of formulae 1 and 2, R and R' represent, the same or different from each other, a group selected from:
—$NHCH_3$,
—$NHCH_2$—CH(OH)—$CH_2OH$,
—$NHCH(CH_2OH)_2$, and
—$N(CH_3)$—$CH_2$—CH(OH)—$CH_2OH$.

From all of the above, as both R and R' groups do not take direct part to the reaction step, as described in details below, it is clear to the skilled person that optional substituent groups, comprised within the meanings of R and R' and which may undergo unwanted side reactions, need to be suitably protected before reaction takes place.

Protection and subsequent deprotection of the said groups can be accomplished by a variety of methods widely known in the art and conventionally adopted in organic synthesis techniques. For a general reference to protective groups in organic chemistry see, for instance, T. W. Green, Protective Groups in Organic Synthesis (Wiley, N.Y. 1981).

The process of the invention is particularly advantageous as it enables the almost exhaustive triiodination of a phenol derivative of formula 1, or of corresponding salt, and leads to a triiodinated derivative of formula 2 that is unaffected, at least to a significant extent, by the presence of side-products deriving from either the partial iodination of the aromatic ring or any other impurity.

Advantageously, therefore, in the process of the invention the purification of the triiodinated compound may be avoided; in fact, it already fulfils the analytical specifications for the industrially produced intermediate in the crude solution, and may therefore be used as such, without isolation and purification in the next reaction step to the final iodinated agent of interest.

As reported above, in the process of the instant invention, the iodination reaction leading to the formation of the triiodophenol compounds of formula 2 occurs by using molecular iodine ($I_2$) in the presence of $HIO_3$, according to the well known electrophilic substitution mechanism.

Under the above conditions, the effective iodinating specie is likely represented by iodine ($I^+$) cations, a portion of which is generated by the added molecular iodine ($I_2$), while the resulting unreactive iodide (I⁻) counter-ions are conveniently oxidized by the HIO₃ back to molecular iodine, or even to iodine cations with a higher oxidation state, thus making them still available for the iodination of the aromatic ring.

Accordingly, the following oxidizing agents able to oxidize the produced iodide (I⁻) ions back to molecular iodine, including, for instance, nitric acid, sulphuric acid, sulphur trioxide, hydrogen peroxide, ozone, and the like, are proposed as an alternative to iodic acid that is, however, especially preferred in the process of the instant invention.

In fact, when molecular iodine is used in the presence of iodic acid, the unreactive iodide ions formed in the iodination reaction are converted back to molecular iodine through the so-called Dushman reaction, according to the following reaction Scheme 1

which further leads to a simultaneous convenient reduction of the iodate (IO₃⁻) ions to molecular iodine, still available for the iodination of the aromatic ring (see, for instance, Furuichi, R. and Liebhafsky, H. A. Radioactive iodine exchange and the Dushman reaction. *Bull. Chem. Soc. Japan* 1973, 46, 2008-2010 and *Bull. Chem. Soc. Japan* 1975, 48, 745-750).

As a result, the complete triiodination of the 3,5-disubstituted phenolic substrate of formula 1 to the desired triiodinated compound of formula 2 is obtained by wholly consuming a stoichiometric amount of iodinating specie, calculated as the sum of both of the added I₂ and HIO₃, and by producing water as the sole reaction by-product, as per the following general reaction Scheme 2.

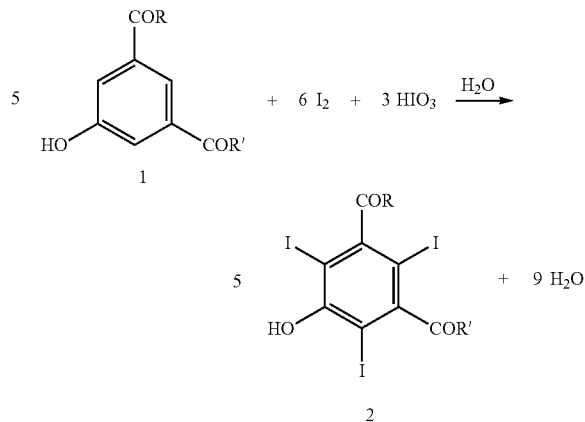

This means that, advantageously, the combined use of iodine and iodic acid, as per the iodination process of the instant invention, makes possible to comprehensively triiodinating the aromatic substrate of formula 1 by avoiding, from one side, the need of any surplus of iodinating agent, especially of molecular iodine and, on the other side, the formation of by-products, especially unreactive poly-iodide ions, for instance of I₃⁻ ions, mainly deriving from the combination of I₂ with iodide ions.

Notably, the sole acid comprised in the iodinating mixture of the present invention is the HIO₃, i.e. a solid acid, commercially available as a ready to use concentrated aqueous solution, that is significantly less strong and easier to handle than HCl used in current industrial iodination processes.

To this extent, it is worth noting that all the acidity related to the iodination process of the present invention, namely the protons either coming from the added HIO₃ or produced during the iodination reaction, are advantageously consumed in said Dushman's redox reaction, as per the above reaction Scheme 1. As a result, very advantageously, the reaction pH is self-maintaining at the desired value during the iodination process, without requiring any exothermic addition of a neutralizing basic solution, and by further preventing any unwanted solution dilution.

In other words, the iodination process of the invention avoids, on one hand, the use of extremely acidic iodinating mixtures, and, on the other, it proceeds by consuming all the acidity associated with the iodination process itself, either deriving from the added iodinating agent or generated by the iodination reaction. Therefore, it allows to overcome the major drawback associated with the iodination processes currently in use, and due, as said, to the need to control and curb the large amount of heat developed in the neutralization reaction with a basic solution, added together with the acidic iodinating mixture, in order to keep the pH of the reaction medium to the desired neutral value.

As a consequence of the above, the process of the instant invention further allows to reduce to a significant extent, from an industrial point of view, the overall time of the iodination process to less than 10 and, preferably, from 5 to 9 total hours.

Furthermore, by avoiding the need of large amount of basic solutions, the process of the instant invention consents to take advantage of higher concentrations (of the crude reaction), and to significantly reduce the amount of produced salts, namely NaCl. This aspect becomes even more relevant to the issue of treatment and disposal of wastewater associated with industrial processes.

From the former general Scheme 2 it follows that the iodination process of the instant invention requires the use of at least 3 moles of iodinating specie, intended, as said, as the sum of both I₂ and HIO₃, for each mol of aromatic substrate 1.

Kept safe this point, in the process of the instant invention the iodination of the phenol substrate is carried out by using at least one mol of molecular iodine for each mol of 3,5-disubstituted phenol of formula 1. Preferably, the molar ratio between iodine and 3,5-disubstituted phenol substrate 1 [I₂/1] will be comprised from 1.1 to 1.3; even more preferably, the triiodination of the 3,5-disubstituted phenol substrate with iodine and iodic acid will be carried out by using 1.2 mol of iodine per mol of substrate 1.

On the other side, because of the stoichiometry of the involved reaction, the molar ratio between I₂ and iodic acid shall be at least equal to 1:0.5, while the molar ratio between iodic acid and 3,5-disubstituted phenol substrate 1 [HIO₃/1] will be comprised from 0.4 to 0.8.

Accordingly, in a particularly preferred embodiment of the invention, the triiodination of the 3,5-disubstituted phenol substrate 1 with iodine and iodic acid will be carried out by using a molar ratio 3,5-disubstituted phenol substrate:iodine:iodic acid of 1:1.2:0.6.

However, a slight excess, for instance of 1% (in mol), over the minimum stoichiometric amount of iodinating agent, intended either as iodine or as iodic acid may, optionally, be used with equally good results, as reported in the experimental section.

To this extent, a minimum amount of sodium bisulfite may, for instance, be added to the final reaction medium in order to destroy any optional residual iodinating species. In this case, the optimal amount (of bisulfite) can, for instance, be potentiometrically determined.

As set forth above, the iodination process of the instant invention, that comprises using the iodinating system I₂/HIO₃, is advantageously carried out in an aqueous medium, for instance water or aqueous solvents, including aqueous saline solutions, or their mixtures with organic solvents such as, for instance, lower alcohols, including methanol or ethanol, dioxane, or glycols, for instance, diethylene glycol or triethylene glycol and methyl ethers thereof. In this latter case, the amount of organic solvent within the aqueous mixture is appropriately chosen so as to not change the total solubility of both the phenolic substrate, or its salt, as well as the triiodinated product, within the crude solution.

Preferred solvents are water and aqueous solutions such as aqueous saline solutions.

To this extent, the use of water, or of an aqueous solvent, compares favourably, in particular from the standpoint of costs and environmental impact, with the use of the organic solvents taught, instead, by the above art using activated iodine as iodinating system.

Moreover, advantageously, the use of an aqueous solvent prevents the need of extracting the substrate compound 1 from the aqueous medium in which it is generally industrially obtained, according to, for instance, EP 185130 or WO 00/32561 procedures, to consents its iodination in the organic medium used, instead, by the cited literature.

Similarly, once obtained, it prevents the need of isolating the iodinated product 2 from the organic crude reaction to may then convert it to the desired radiographic agent in the aqueous medium commonly used in the industrial processes today in use.

Figure 3:
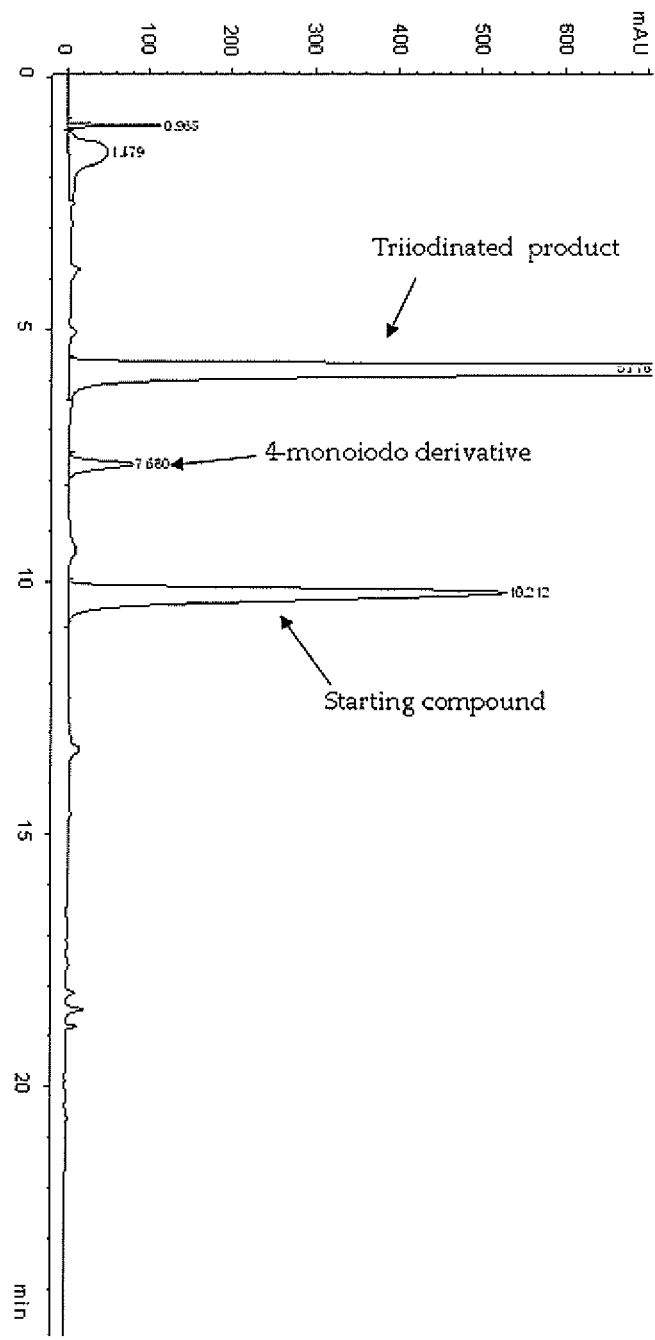
FIG. 3: Comparative Example 1: chromatogram (HPLC) of the crude solution after 1.5 hours at 38-40° C.
Figure 4:
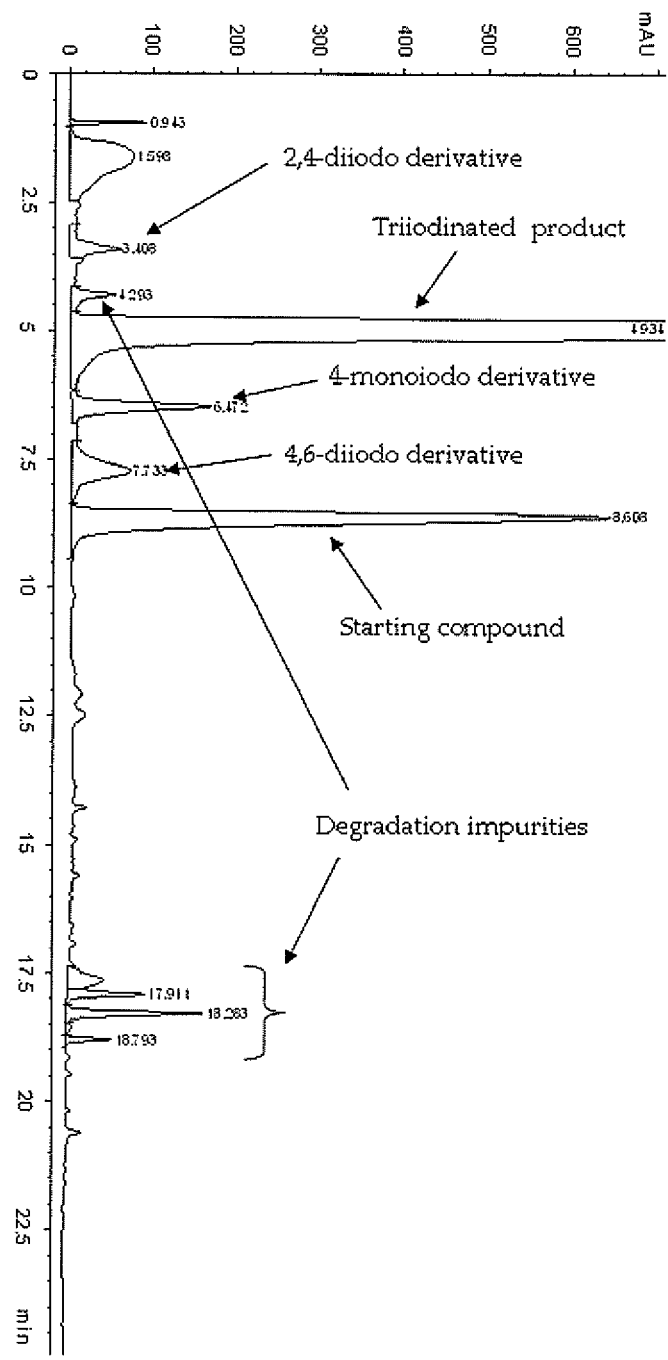
FIG. 4: Comparative Example 1: HPLC of the crude solution after 3.5 hours at 38-40° C.
Figure 5:
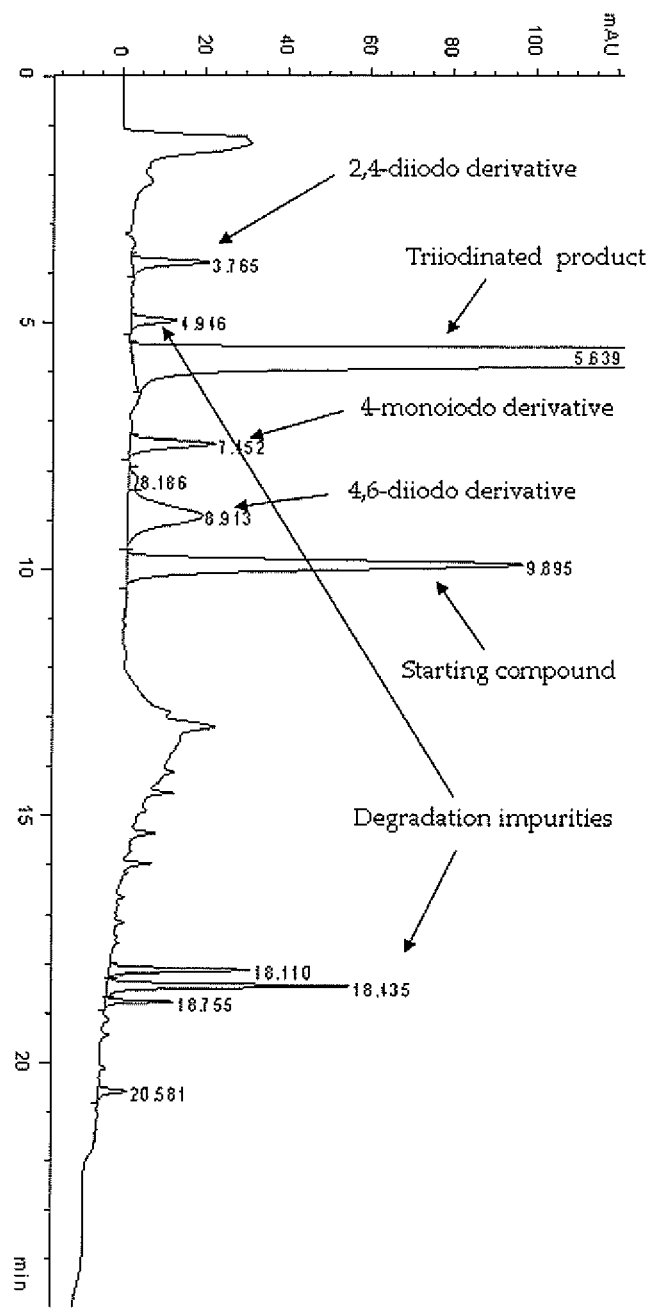
FIG. 5: Comparative Example 1: HPLC of the mother liquors after precipitation of the triiodinated product.

Unexpectedly, moreover, the use of an aqueous solvent, as per the process of the instant invention, allows to solve the problem of the low reaction yield obtained by the cited art using activated iodine in an organic solvent, and confirmed by the Comparative Example 1 of the following experimental section, which is most likely ascribable to both an incomplete conversion of the aromatic substrate and the good solubility of the tri-iodinated product into the elected alcoholic medium, that prevents its exhaustive precipitation or crystallization from the crude solution, as shown in FIGS. 3-5.

Figure 2:
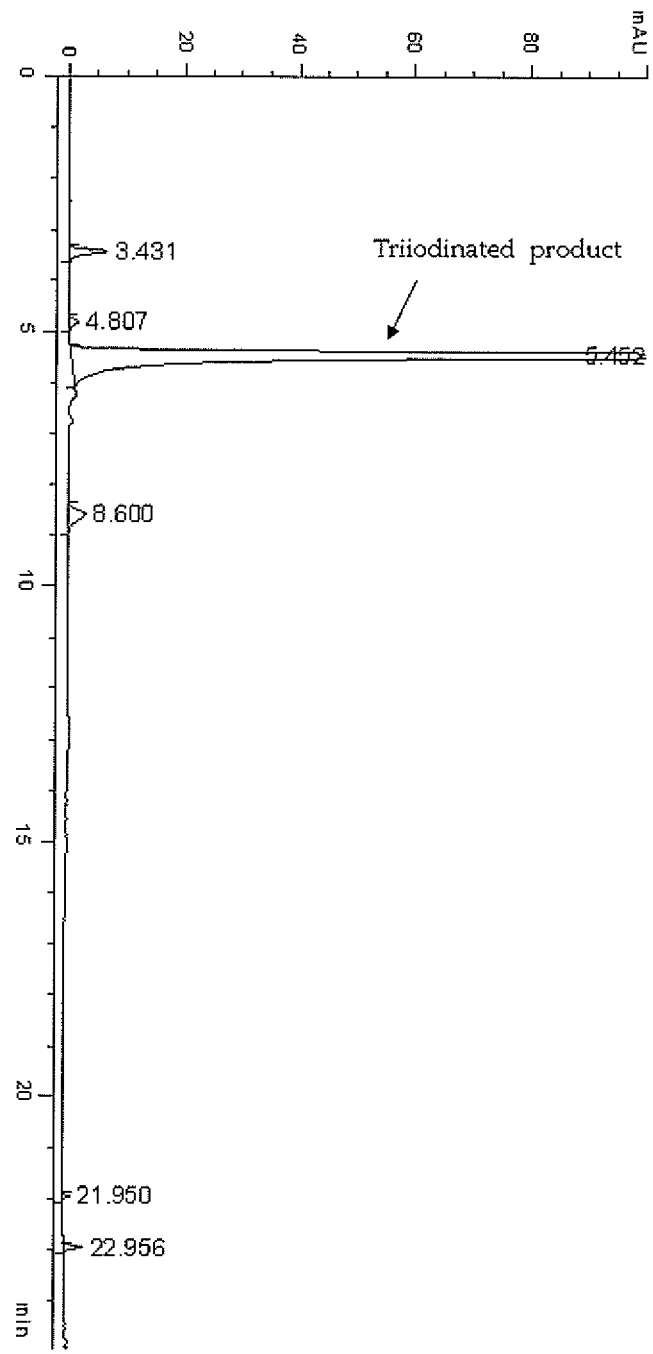
FIG. 2: Example 6: HPLC of the crude solution after 6 hours of reaction (final solution).

In fact, the use of an aqueous solvent according to the process of the instant invention enables the almost exhaustive tri-iodination of the aromatic substrate and leads to a triiodinated product that is substantially pure in the crude solution, as appears from FIGS. 1 and 2. As a result, the process of the invention does not require any isolation and purification step of the iodinated compound that, being obtained with very good yield and high purity in the crude solution, may be used as such in the next reaction step to the final iodinated agent. Therefore, any possible loss of iodinated product resulting from its isolation and/or purification may advantageously be avoided.

From all the above, and according to an especially preferred embodiment of the invention, the triiodination of the 3,5-disubstituted phenol substrate with iodine and iodic acid is carried out directly on the crude aqueous solution deriving from the industrial process for the preparation of the desired contrast agent, in which the phenol substrate is commonly comprised as sodium salt.

The iodination process of the instant invention essentially comprises: obtaining an aqueous solution of the 3,5-disubstituted phenol substrate of formula 1, or of a salt thereof, used as starting material, and adding solid $I_2$ and $HIO_3$ to said solution.

During the process, the temperature is kept lower than 70° C., preferably comprised from 20 to 70° C., and, more preferably from 40 to 60° C.

More particularly, main steps of the process of the instant invention include:

I) obtaining an aqueous solution of a 3,5-disubstituted phenol substrate of formula 1, or of a salt thereof, that is used as starting material, II) adding solid $I_2$ to said aqueous solution heated to a temperature comprised from 20 to 70° C., and then III) adding iodic acid.

In one embodiment of the invention, the step I) of the above process comprises obtaining a solution of the 3,5-disubstituted phenol substrate of formula 1, or of a salt thereof, used as pure compound, into an aqueous solvent, typically water, and using this solution as starting material. Preferably, the said starting solution has a concentration comprised from 24 to 10% (w/w), and a pH comprised from 9 to 10.

To this extent, and unless otherwise provided in the present description, suitable salts of the phenol substrate of formula 1 are preferably selected from alkali or alkali-earth metal salts of the substrate such as, for instance, sodium, lithium, potassium, calcium or magnesium salts.

Particularly preferred, among them, is the sodium salt of the 3,5-disubstituted phenol substrate, which can be used as such, i.e. as a pure compound or, alternatively, as comprised within a crude solution directly deriving from an industrial process, typically for the preparation of triiodinated contrast agents, e.g. Iomeprol, for instance carried out as disclosed in WO00/32561. According to an especially preferred embodiment of the instant invention, the aqueous solution used as starting material is a crude aqueous solution directly obtained from an industrial process for the preparation of the desired contrast agent, commonly comprising the starting 3,5-disubstituted phenol substrate as sodium salt at a concentration ranging from 20 to 25% (w/w).

In this case, the said crude solution, that generally has a pH comprised from 9 to 10, may be used as such or, optionally, after dilution, typically with water, for instance up to half the original concentration.

Solid $I_2$ is then added to the phenol substrate solution previously heated to a temperature lower that 70° C., preferably comprised from 20 to 70° C., and, more preferably, from 30 to 60° C. To this extent, it should be clear to a skilled practitioner that as soon as the iodine is added to the heated solution of the phenol substrate, the iodination reaction occurs through the well known electrophilic substitution mechanism, for instance started by the $I^+$ ions generated by the added iodine, thus generating $H^+$ ions. As a result, the pH of the reaction mixture decreases from the original basic values, to values even below neutrality.

The proper amount of the iodic acid is then added to the reaction mixture.

In this regard, $HIO_3$ is preferably added to the crude solution when the pH of the reaction medium reaches a value comprised from 4.5 to 7 and, preferably, from 5 to 6. In an especially preferred embodiment of the instant invention, the proper amount of iodic acid is added to the reaction medium when the latter reaches a pH value comprised from 5 to 5.5.

Interestingly, in fact, despite it is well known in the art that the electrophilic substitution reaction is significantly activated on phenols that are in the deprotonated (phenate) form, and that the molar ratio of this latter (over the phenol substrate) increases with the increase of the solution pH, we have found that under the identified pH conditions, apparently unfavourable, 3,5-disubstituted-2,4,6-triiodophenol derivatives of formula 2 are, instead, unexpectedly obtained with higher yield and purity.

To this extent, the proper amount of iodic acid may be added to the reaction mixture at once or, alternatively, gradually, in a time of up to 4 hours, either continuously over time or portion-wise according to conventional means, thus causing the progressive conversion of the substrate compound into the corresponding triiodinated derivative. More particularly, and according to the following experimental section, iodic acid may be added quickly, for instance in a time of up to a couple of hours, to starting solutions heated to temperatures for instance comprised from 55 and 65° C. and preferably to about 60° C. Instead, when the starting solution is heated to a lower temperature, for instance comprised from 20 to 50° C. and, a slower addition of iodic acid is preferable, that may be effected over a time of up to 4 hours.

In this respect, an aqueous solution of the oxidizing agent can profitably be used, with a concentration comprised, for instance, from 30 to 35% (w/w).

Interestingly, when operating under the above conditions, the pH of the reaction mixture is self-maintaining at the desired value, namely comprised from 5 to 5.5, during all the $HIO_3$ addition time and the subsequent completion time, without requiring any correction with acid or basic solutions.

This interestingly allows to reduce to a minimum extent all partially iodinated by-products, as well as all those impurities, for instance due to the possible iodine dismutation, favoured in alkaline environments, or to the optional over-concentration of the $HIO_3$, and/or the excessively increased oxidative power thereof, favoured, instead, at lower pH.

As a result, a triiodinated product of formula 2 is obtained in the crude solution with good yields and high purity, preferably equal or greater that 98%, that may, therefore, be used as such in the next step to the desired radiographic contrast agent, without requiring any isolation and further purification.

In this respect, the purity of the triiodinated compound within the final crude solution may be chromatographically determined, for instance by means of the HPLC technique, either as area % or versus a standard, that generally consists of the pure isolated 3,5-disubstituted-2,4,6-triiodophenol.

Though the isolation of the triiodinated product of formula 2, if desired, is obtainable through methods known in the organic chemistry, for instance comprising the use of ion exchange resins or electrodialysis or by membrane based filtration and concentration of the crude solution, according to a particularly preferred embodiment of the invention the crude solution of the triiodinated product of formula 2 obtained by using the iodination process of the instant invention is used as such, in the next reaction step to the desired radiographic agent, without undergoing any previous isolation or further purification of the iodinated compound it comprises.

By working at the above mentioned temperatures, the process should not lead to significant losses, by evaporation, of the aqueous solvent. The heating of the crude reaction at higher temperatures might, instead, optionally lead to a partial sublimation of the molecular iodine. However, by keeping the reaction temperature in the range of values formerly referred, the iodination process normally proceeds without significant loss of this reactant. Nevertheless, conventional cooling or condensing equipments may also be used to condensate the sublimated iodine that is then added to the reaction, optionally through a small amount of solvent.

Details on the process of the invention are reported in the following Experimental Section, for instance through Examples 1-7 concerning the iodination of 3,5-disubstituted phenols according to the present invention.

However, from operative point of view, main steps and preferred conditions of the claimed process are schematically reported below.

For instance, in one option, solid $I_2$ is added to a solution of 3,5-disubstituted phenol substrate, or of a salt thereof, or to a basic crude solution of the latter, directly obtained from the industrial process for the preparation of the desire radiographic agent, previously heated to a temperature comprised from 55 to 65° C. and, preferably, about 60° C.

Aqueous $HIO_3$ is then loaded in the obtained mixture in about two hours, starting from when the pH of the reaction mixture is about 5. The reaction mixture is then maintained under stirring and at the above temperature for additional 4 hours (completion time), and then cooled down to 25° C. Whole reaction time: about 6 hours. Alternatively, first $I_2$ and then $HIO_3$ (at the above pH value of the reaction mixture) may be loaded in the starting solution heated to about 40° C., In this case the addition of $HIO_3$ is preferably made in a time of about 3 hours. The reaction temperature is then raised to 50° C., and maintained to this value for 1 hour, then to about 60° C. for 1 additional hour before to be cooled down to 25° C. (total reaction time: 7 hours). Again, the iodinating agents ($I_2$ and $HIO_3$) are both added to a reaction mixture heated to about 30° C. ($HIO_3$ addition time about 4 hours), and the reaction temperature is then raised and maintained from 55 to 65° C. for additional 4 hours before to be cooled to room temperature (total reaction time: 8 hours), or, still otherwise, $I_2$ is loaded in the starting solution at room temperature (about 20° C.), the mixture is then heated to 40° C. and loaded, in about 4 hours, with $HIO_3$, the crude reaction is then raised to 60° C. over 2 hours and kept to this value for additional 4 hours before to be cooled down to room temperature (total reaction time: 9 hours).

A minimum amount of 18% (w/w) aqueous solution of sodium bisulfite may then be optionally added to the cooled mixture in order to destroy any optional residual iodinating species. To this extent, the optimal amount can, for instance, be potentiometrically determined as the minimum amount of bisulfite that leads to a redox potential of the final mixture (kept to pH 5) to a stable negative value comprised from 0 to −20 mV.

Alternatively, to facilitate the reading of the redox potential variation, the crude solution may be first adjusted and maintained to pH 7 with 30% (w/w) aqueous NaOH, then quenched with an aqueous solution of sodium bisulfite until a redox potential comprised, in this case, from −20 to −50 mV.

The compounds of formula 1 used as starting material of the process of the invention are known and, if not commercially available per se, may be all prepared according to known methods. In this respect, as a general reference see, for instance, the aforementioned EP 185130 and WO 00/32561. Likewise, any other reactant and/or solvent being employed in the instant process is known and readily available.

Once obtained, the 3,5-disubstituted-2,4,6-triiodophenol derivatives of formula 2 may be then easily converted into the corresponding radiographic contrast agents of interest.

Hence, a further object of the present invention is a process for the preparation of a compounds of formula 5

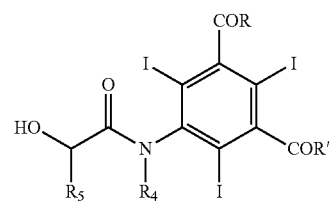

in which:
R and R', the same or different from each other, are as formerly defined, and $R_4$ and $R_5$ are, the same or different from each other, hydrogen or a straight or branched $C_1$-$C_6$ alkyl group, optionally substituted by one or more hydroxyl group or $C_1$-$C_6$ alkoxy groups,
said process comprising the preparation of the 3,5-disubstituted-2,4,6-triiodophenol derivatives of formula 2 by iodinating a 3,5-disubstituted phenol substrate of formula 1, or a salt thereof, with molecular iodine in the presence of HIO$_3$ through the process of the instant invention, substantially as described above.

More preferably, said process comprises:
a) iodinating a 3,5-disubstituted phenol substrate of formula 1, or a salt thereof, in an aqueous medium, with molecular iodine in the presence of HIO$_3$ to obtain the corresponding 2,4,6-triiodophenol derivative of formula 2; the said process further comprises:
b) reacting the obtained compound of formula 2, wherein the phenolic OH group may optionally be in the form of a salt with an alkali metal, with a compound of formula 3

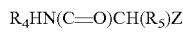

R$_4$HN(C=O)CH(R$_5$)Z  3 wherein R$_4$ and R$_5$ are, the same or different from each other, as defined above, and Z is a halogen atom, such as Cl, Br, I and, preferably, Cl or Br, or any suitable leaving group such as, for instance, a residue of a sulfonic acid (for instance methanesulfonyloxy (MeSO$_2$O$^-$), benzenesulfonyloxy (PhSO$_2$O$^-$), nitrobenzenesulfonyloxy (p-NO2PhSO$_2$O$^-$), toluensulfonyloxy (TsO$^-$), and so on), and, preferably, toluensulfonyloxy; so as to obtain a compound of formula 4

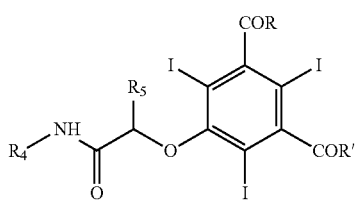

4 wherein R, R', R$_4$ and R$_5$ have the above reported meanings; and
c) subjecting the compound of formula 4 to Smiles's rearrangement in the to presence of a base so as to obtain the desired final compound of formula 5

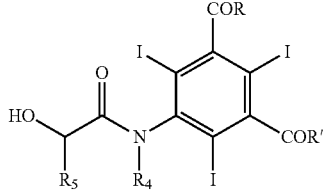

5

According to said process for preparing x-ray contrast agents, the iodination step a) is carried out as extensively reported above, by the process of the instant invention, while subsequent steps, b) and c) comprehensive of experimental conditions and optional variants thereof, are known in the art and described, for instance, in the patent applications WO97/05097, WO 88/09328, EP 185130 and WO 00/32561.

Preferably, the instant process may be applied for the preparation of radiographic agents within the compound of formula 5 in which R and R' represent, the same or different form each other, a group selected from:
—NHCH$_3$,
—NHCH$_2$—CH(OH)—CH$_2$OH,
—NHCH(CH$_2$OH)$_2$, and
—N(CH$_3$)—CH$_2$—CH(OH)—CH$_2$OH,
and R$_4$ and R$_5$ are, the same or different from each other, hydrogen or a methyl group. Even more preferably, the instant process may be applied to the preparation of widely known x-ray contrast agents like Iopoamidol (wherein, respectively, R and R' both represent a —NH—CH(CH$_2$OH)$_2$ group, R$_4$ is hydrogen and R$_5$ is methyl; see The Merck Index, XIII Ed., 2001, No. 5073) or Iomeprol (wherein, respectively, R and R' both represent a —NH—CH$_2$—CH(OH)CH$_2$OH group, R$_4$ is methyl and R$_5$ is hydrogen; see The Merck Index, XIII Ed., 2001, No. 5071).

Therefore, a further embodiment of the instant invention is a process for the preparation of Iopamidol or Iomeprol that is characterized in that it comprises starting from the compounds of formula 2a or 2b, respectively obtained by iodination of the corresponding substrate compounds of formula 1a and 1b with molecular iodine in the presence of iodic acid, according to the process of the present invention.

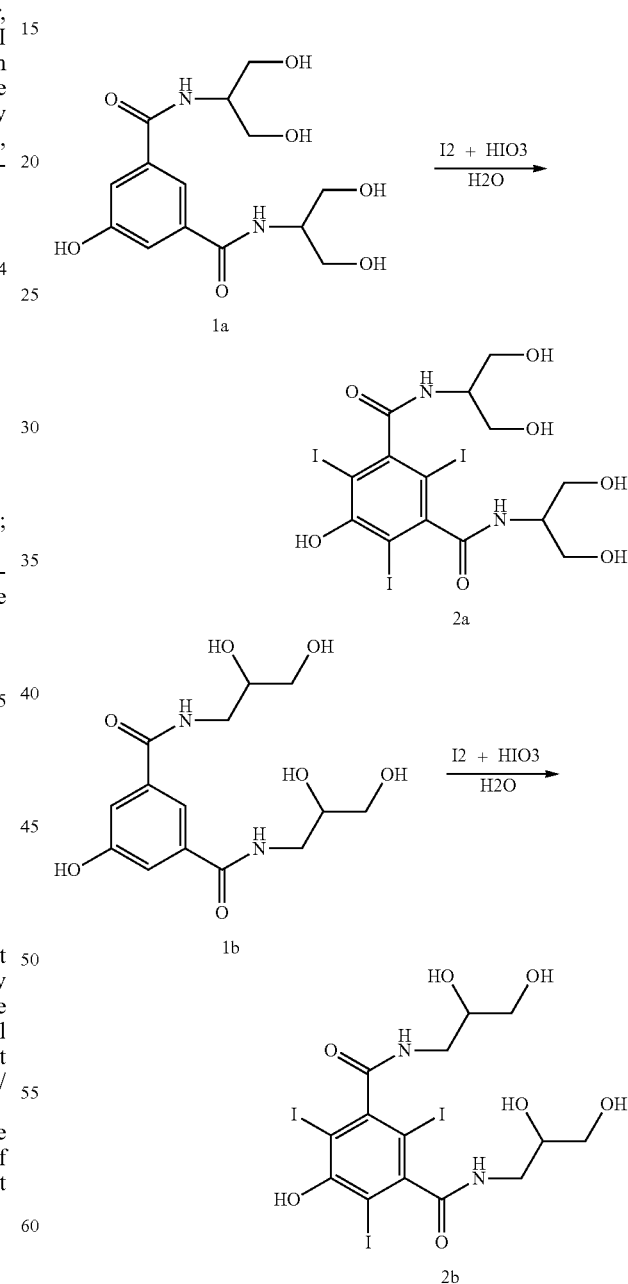

In particular, the process for the preparation of Iomeprol comprises, essentially, the steps represented in the following Scheme 3:

Scheme 3

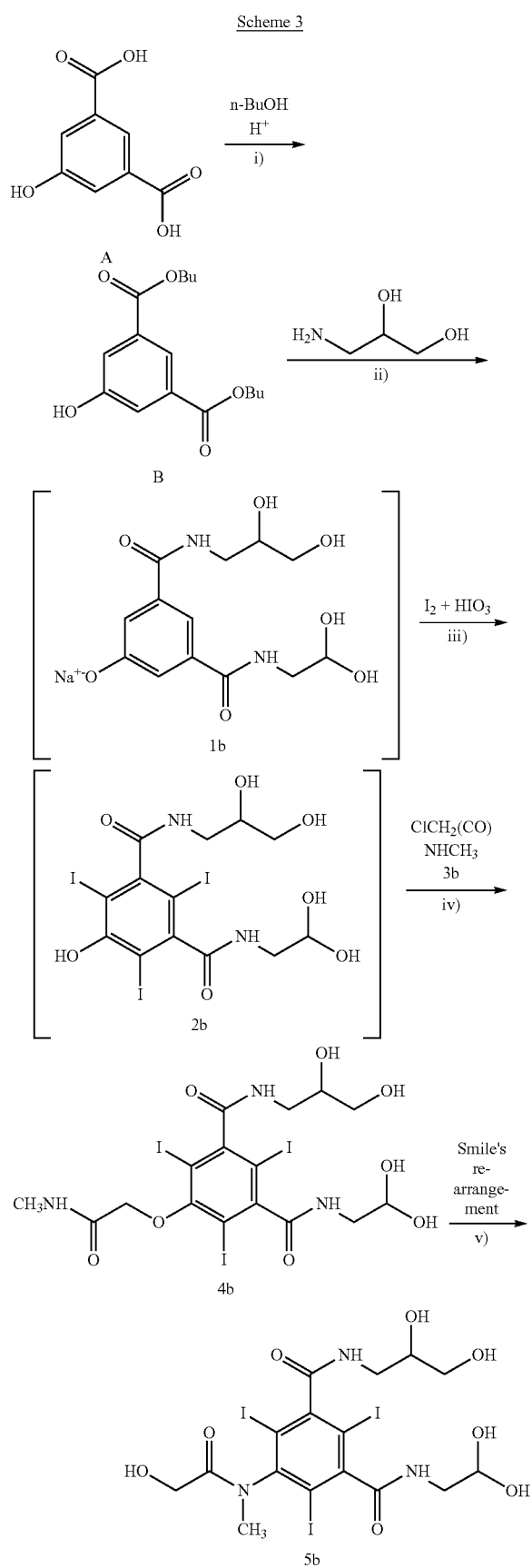

and is characterized in that the iodination step iii) is carried out with molecular iodine in the presence of iodic acid and by operating in continuous, that is to say directly on the crude solution of the compound of formula 1b obtained from the former step ii) of the process, to give a crude solution of the iodinated compound of formula 2b used as such in the next alkylation step iv) to the intermediate 4b without isolation or purification of any of the involved intermediates.

In the above process, the step iii) is carried out according to the iodination process of the instant invention, as extensively reported above, while steps, i), ii), iv) and v), comprehensive of experimental conditions and optional variants thereof, are carried out according, for instance, to WO 00/32561 and cited references.

In this respect, preferred Smiles's rearrangement conditions in step v) of the process, comprising the use of a base such as aqueous NaOH, and purification of the final agent are, for instance, disclosed in EP365,541.

Further details concerning the iodination process of the instant invention are reported in the following experimental section, with the sole aim to better illustrate the present invention, without representing any limitation to it.

EXPERIMENTAL SECTION

Characterization of the Obtained Compounds.

The purity of the obtained 3,5-substituted-2,4,6-triiodophenols and their derivatives have been determined by HPLC using the pure compound as standard.

General Procedure

HPLC Chromatographic Method

Stationary phase: Zorbax SB C18, 3.5 µm, 150×4.6 mm (Agilent Technologies)

Mobile phase: A: 0.010 M $KH_2PO_4$+0.1% $H_3PO_4$
B: MeOH

Elution: gradient elution
gradient table:

| t (min) | phase A (%) | phase B (%) |
|---|---|---|
| 0 | 97 | 3 |
| 10 | 97 | 3 |
| 16 | 60 | 40 |
| 25 | 10 | 90 |
| 32 | 10 | 90 |

Temperature: 45° C.
Detection: UV (240-300 nm)
Flow: 1.5 L/min
Sample concentration: 1 mg/mL
Injection: 10 µL

Example 1

Preparation of a Compound of Formula 2 Wherein R and R' Both are a —NH—$CH_2$—CH(OH)$CH_2$OH Group Using a Starting Solution Heated at 60° C.

In a 2 L four-necked jacket reactor equipped with mechanical stirrer, condenser and combined pH/temperature electrode, an aqueous solution of 3,5-disubstituted phenol 1 sodium salt, corresponding to 22.8% (w/w) of phenol, (1175 g of solution; 0.816 mol; pH 9.6) was heated at 60° C. then solid $I_2$ (250.6 g; 0.988 mol) was added in one portion. When the pH spontaneously decreased to 5, a 50% (w/w) aqueous solution of $HIO_3$ (173.6 g; 0.494 mol) was slowly added over 2 h. The reaction mixture was maintained at 60° C. for additional 4 h in the meanwhile the pH spontaneously remained at 5-5.5. The red solution was cooled to 25° C. and quenched by addition of an 18% (w/w) aqueous solution of sodium bisulfite until decolourisation and the redox potential, measured with a suitable redox electrode, reached a stable negative value ranging from 0 to −20 mV.

During the quenching, the reaction mixture is kept to pH 5 by addition of minimum amounts of 30% (w/w) aqueous solution of NaOH.

The HPLC analysis (reported in FIG. 1) indicated a conversion to 3,5-disubstituted-2,4,6-triiodophenol 2b >98% (HPLC area %) and the solution was used in the following synthetic step without any further treatment.

Example 2

Preparation of a Compound of Formula 2 Wherein R and R' Both are a —NH—$CH_2$—CH(OH)$CH_2$OH Group Using a Starting Solution Heated at 40° C.

In a 2 L four-necked jacket reactor equipped with mechanical stirrer, condenser and combined pH/temperature electrode, solid $I_2$ (250.6 g; 0.988 mol) was added in one portion to an aqueous solution of 3,5-disubstituted phenol 1 sodium salt corresponding to 22.8% (w/w) of phenol (1175 g of solution; 0.816 mol; pH 9.6) heated at 40° C. When the pH spontaneously decreased to 5, a 50% (w/w) aqueous solution of $HIO_3$ (173.6 g; 0.494 mol) was slowly added over 3 h. The reaction mixture was then heated 2 h at 40° C., 1 h at 50° C. and 1 h at 60° C. during which the pH spontaneously remained at 5-5.5. The red solution was cooled to 25° C., adjusted and maintained at pH 7 with 30% (w/w) aqueous solution of NaOH during the quenching performed by addition of an 18% (w/w) aqueous solution of sodium bisulfite until decolourisation and the redox potential, measured with a suitable redox electrode, reached a stable negative value ranging from −20 to −50 mV.

The HPLC analysis indicated a conversion to 3,5-disubstituted-2,4,6-triiodophenol 2b >98% (HPLC area %) and the solution was used for the following synthetic step without any further treatment.

Example 3

Preparation of a Compound of a Formula 2 Wherein R and R' Both are —NH—$CH_2$—CH(OH)$CH_2$OH Group Using a Starting Solution Heated at 30° C. and Final Quenching with Bisulfite at pH 5

In a 4 L four-necked jacket reactor equipped with mechanical stirrer, condenser and combined pH/temperature electrode, an aqueous solution of 3,5-disubstituted phenol 1 sodium salt, corresponding to 22.8% (w/w) of phenol (1175 g of solution; 0.816 mol; pH 9.6) was diluted with $H_2O$ (1054 g), heated at 30° C., and then added with solid $I_2$ (250.6 g; 0.988 mol) in one portion. When the pH spontaneously decreased to 5, a 50% (w/w), aqueous solution of $HIO_3$ (173.6 g; 0.494 mol) was slowly added over 4 h. The reaction mixture was raised to 60° C. and maintained to this value for additional 4 h, in the meanwhile the pH spontaneously remained at 5-5.5. The red solution was cooled to 25° C. and quenched by addition of an 18% (w/w) aqueous solution of sodium bisulfite, maintaining pH 5 by addition of 30% (w/w) aqueous solution of NaOH, until decolourisation and the redox potential, measured with a suitable redox electrode, reached a stable negative value ranging from 0 to −20 mV.

The HPLC analysis indicated a conversion to 3,5-disubstituted-2,4,6-triiodophenol 2b >98% (HPLC area %) and the solution was used in the following synthetic step without any further treatment.

Example 4

Preparation of a Compound of Formula 2 Wherein R and R' both are a —NH—$CH_2$—CH(OH)$CH_2$OH Group Using a Starting Solution Heated at 30° C. and Final Quenching with Bisulfite at pH 7

In a 4 L four-necked jacket reactor equipped with mechanical stirrer, condenser and combined pH/temperature electrode, an aqueous solution of 3,5-disubstituted phenol 1 sodium salt corresponding to 22.8% (w/w) of phenol (1175 g of solution; 0.816 mol; pH 9.6) was diluted with $H_2O$ (1054 g), heated at 30° C. and then added with solid $I_2$ (250.6 g; 0.988 mol) in one portion. When the pH spontaneously decreased to 5, a 50% (w/w) aqueous solution of $HIO_3$ (173.6 g; 0.494 mol) was slowly added over 4 h. The reaction mixture was then raised to 60° C. and maintained to this temperature for additional 4 h in the meanwhile the pH spontaneously remained at 5-5.5. The red solution was cooled to 25° C., adjusted and maintained at pH 7 with 30% (w/w) aqueous solution of NaOH during the quenching performed by addition of an 18% (w/w) aqueous solution of sodium bisulfite until decolourisation and the redox potential, measured with a suitable redox electrode, reached a stable negative value ranging from −20 to −50 mV.

The HPLC analysis indicated a conversion to 3,5-disubstituted-2,4,6-triiodophenol 2b >98% (HPLC area %) and the solution was used in the following synthetic step without any further treatment.

Example 5

Preparation of a Compound of Formula 2 Wherein R and R' Both are a —NH—$CH_2$—CH(OH)$CH_2$OH Group Using a Staring Solution Kept at Room Temperature (About 20° C.).

In a 4 L four-necked jacket reactor equipped with mechanical stirrer, condenser and combined pH/temperature electrode, an aqueous solution of 3,5-disubstituted phenol 1 sodium salt corresponding to 22,8% (w/w) of phenol (1175 g of solution; 0.816 mol; pH 9.6) kept to 20° C., was firstly diluted with $H_2O$ (1054 g) and then added, in one portion, with solid $I_2$, (250.6 g; 0.988 mol). The resulting solution was then heated to 40° C. and, when the pH spontaneously decreased to 5, a 50% (w/w) aqueous solution of $HIO_3$ (173.6 g; 0.494 mol) was slowly added over 4 h. Then, the crude solution was raised to 60° C. over 2 h, and maintained at 60° C. for additional 3 h; in the meanwhile the pH spontaneously remained at 5-5,5. The red solution was hence cooled to 25° C., adjusted and maintained at pH 7 with 30% (w/w) aqueous NaOH and quenched with sodium bisulfite (a 18% (w/w) aqueous solution) until decolourisation and stable negative value (ranging from −20 to −50 mV) of the redox potential, measured with a suitable redox electrode.

The HPLC analysis indicated a conversion to 3,5-disubstituted-2,4,6-triiodophenol 2b >98% (HPLC area %) and the solution was used in the following synthetic step without any further treatment.

Example 6

Preparation of a Compound of Formula 2 Wherein R is —NH—CH$_2$—CH(OH)CH$_2$OH and R' is —NH—CH(CH$_2$OH)$_2$ Using a Starting Solution Heated at 60° C.

In a 1 L four-necked jacket reactor equipped with mechanical stirrer, condenser and combined pH/temperature electrode, N-(2,3-dihydroxypropyl)-N'-[2-hydroxy-1-(hydroxymethyl)ethyl]-5-hydroxy-1,3-benzendicarboxamide (100.3 g; 0.305 mol) was dissolved in H$_2$O (430 g) and converted into corresponding sodium salt by addition of 30% (w/w) NaOH (40.6 g; 0.305 mol) (pH 9.5). The solution was heated at 60° C. and solid I$_2$ (93.1 g; 0.367 mol) was added in one portion; when the pH spontaneously decreased to 5, a 50% (w/w) aqueous solution of HIO$_3$ (64.5 g; 0.183 mol) was slowly added over 2 h. The reaction mixture was maintained at 60 ° C. for additional 4 h in the meanwhile the pH spontaneously remained at 5-5.5. The red solution was cooled to 25° C. and quenched by addition of an 18% (w/w) aqueous solution of sodium bisulfite, maintaining pH 5 by addition of 30% (w/w) aqueous solution of NaOH, until decolourisation and the redox potential, measured with a suitable redox electrode, reached a stable negative value ranging from 0 to −20 mV.

The HPLC analysis (FIG. 2) indicated a conversion to N-(2,3-dihydroxypropyl)-N'-[2-hydroxy-1-(hydroxymethyl)ethyl]-5-hydroxy-2,4,6-triiodo-1,3-benzendicarboxamide >98% (HPLC area %) and the solution was used in the following synthetic step without any further treatment.

Example 7

Preparation of a Compound of Formula 2 wherein R and R' Both are —NH—CH(CH$_2$OH)$_2$ Using a Starting Solution Heated at 60° C.

In a 0.5 L four-necked jacket reactor equipped with mechanical stirrer, condenser and combined pH/temperature electrode, N,N'-bis[2-hydroxy-1-(hydroxymethyl)ethyl]-5-hydroxy-1,3-benzendicarboxamide (50 g; 0.152 mol) was dissolved in H2O (215 g) and converted into corresponding sodium salt by addition of 30% (w/w) NaOH (20.3 g; 0.152 mol) (pH 9.5). The solution was heated at 60° C. and solid I$_2$ (46.4 g; 0.183 mol) was added in one portion; when the pH spontaneously decreased to 5, a 50% (w/w) aqueous solution of HIO$_3$ (32.2 g; 0.091 mol) was slowly added over 2 h. The reaction mixture was maintained at 60° C. for additional 4 h in which the pH spontaneously remained at 5-5.5. The red solution was cooled to 25° C. and quenched by addition of a 18% (w/w) aqueous solution of sodium bisulfite, by maintaining pH 5 with 30% (w/w) aqueous NaOH, until decolourisation and stable negative value (ranging from −20 to −50 mV) of the redox potential, measured with a suitable redox electrode.

The HPLC analysis indicated a conversion to N,N'-bis[2-hydroxy-1-(hydroxymethyl)ethyl]-5-hydroxy-2,4,6-triiodo-1,3-benzendicarboxamide >98% (HPLC area %) and the solution was used in the following synthetic step without any further treatment.

Comparative Example 1

This test was performed to evaluate the exploitability of the iodinating conditions disclosed by Patil et al, in *ARKIVOC*, 2006, 104 and *Tetrahedron Lett.*, 2005. 46, 7179.

In a 50 mL three-necked round bottom flask equipped with thermometer and condenser solid 3,5-disubstituted phenol 1 (16.4 g; 50 mmol) was suspended in ethanol (30 mL). To the obtained suspension, heated at 38-40° C., were then added, respectively, solid I$_2$ (15.2 g; 60 mmol) in one portion, and a solution of HIO$_3$ (5.3 g; 30 mmol) in H$_2$O (3 mL) over 5 min. The resulting dark brown mixture was maintained under stirring at 38-40° C. for around 1 h before registering the change of the reaction mixture into a clear dark brown solution. The reaction mixture was kept at the above temperature conditions for a total of 3.5 h, then cooled to room temperature thus promoting the crystallization of a pale yellow solid product. After 15 h at room temperature the solid was filtered and dried to give the desired 3,5-disubstituted-2,4,6-triiodophenol (12.1 g; 17 mmol). Yield 34.3%.

The iodination reaction was followed and analysed by HPLC. In particular, a first check was performed 1.5 h after the iodination beginning, (reaction time suggested by the cited art), reported in FIG. 3, and a second one after additional 2 hours (total reaction time 3.5 hours), reported in FIG. 4. Obtained results show that even after 3.5 h the conversion is not complete and a significant amount (13%, HPLC area %) of starting substrate is still present. On the other side, more prolonged reaction times lead to the formation of significant amount of degradation impurities, already well detectable after 3.5 hours reaction (FIG. 4). This is undoubtedly a factor that adversely affects the yields. However, the poor reaction yield is also ascribable to the solubility of the 3,5-disubstituted-2,4,6-triiodophenol 2b in the alcoholic medium, confirmed by the analysis of the mother liquor shown in FIG. 5, that prevents the quantitative recovery of the iodination product.

To this extent, the improvement in both reaction yield and product purity resulting from the use of an aqueous medium and the operative conditions settled forth in the foregoing results apparent when comparing FIGS. 3-5 with FIGS. 1 and 2, reporting, instead, the chromatogram (HPLC) of the crude solution (of Examples 1 and 6, respectively) obtained by using the process of the instant invention.

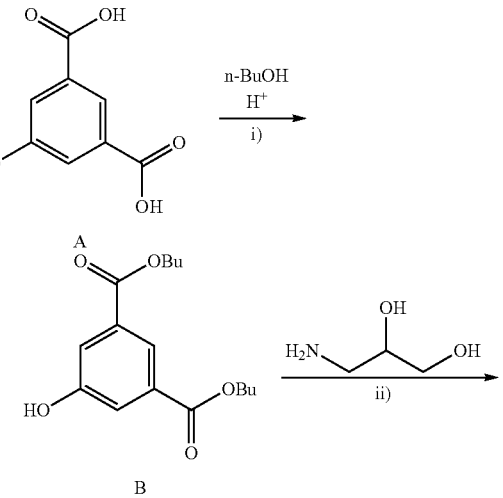

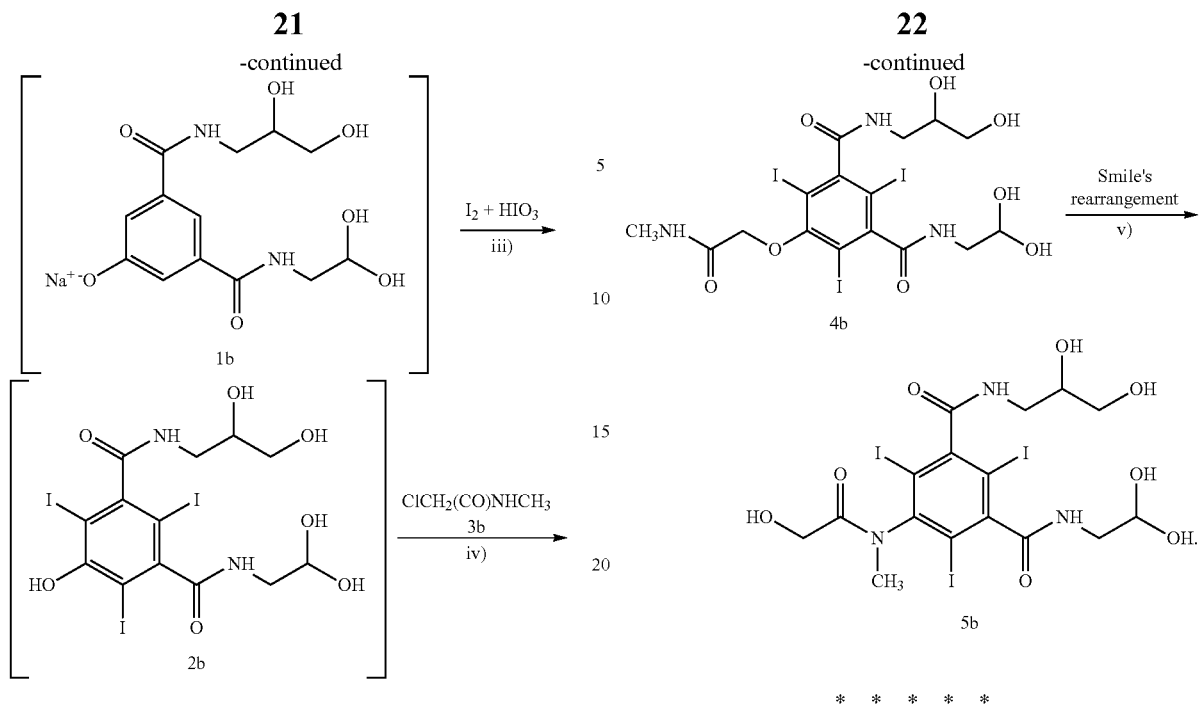

The invention claimed is:

1. A process for the preparation of triiodophenol compounds of formula 2

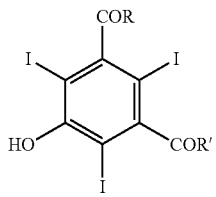

comprising the iodination of a 3,5-disubstituted phenol of formula 1,

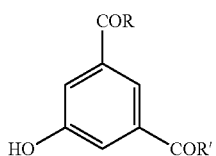

or a salt thereof, in an aqueous medium, with molecular iodine in the presence of iodic acid, wherein:

R and R' represent, independently, a group of formula —NHR$_1$ or —NR$_2$R$_3$, wherein each R$_1$, R$_2$ and R$_3$ is, independently, a straight or branched C$_1$-C$_6$ alkyl group which is optionally substituted by one or more groups selected from hydroxyl (—OH), $C_1$-$C_5$ alkoxy and hydroxyalkoxy groups.

2. The process of claim 1 wherein, within the compounds of formulae 1 and 2, R and R' represent, independently, a group of formula —$NHR_1$ or —$NR_2R_3$ wherein each $R_1$, $R_2$ and $R_3$ is, independently, a straight or branched $C_1$-$C_4$ alkyl group optionally substituted by one to three hydroxyl groups.

3. The process of claim 2 wherein, within the compounds of formulae 1 and 2, R and R' represent, independently, a group selected from:
—$NHCH_3$,
—$NHCH_2$—CH(OH)—$CH_2OH$,
—$NHCH(CH_2OH)_2$, and
—$N(CH_3)$—$CH_2$—CH(OH)—$CH_2OH$.

4. The process of claim 1 wherein the molar ratio between molecular iodine and 3,5-disubstituted phenol substrate 1 [$I_2$/1] is comprised from 1.1 to 1.3, and the molar ratio between iodic acid and 3,5-disubstituted phenol substrate 1 is comprised from 0.4 to 0.8.

5. The process according to claim 4 wherein the triiodination of the 3,5-disubstituted phenol substrate 1 with iodine and iodic acid is carried out by using a molar ratio 3,5-disubstituted phenol substrate:iodine:iodic acid of 1:1.2:0.6.

6. The process according to claim 1 wherein said aqueous medium is water or an aqueous solution.

7. The process of claim 6 comprising: obtaining an aqueous solution of 3,5-di-substituted phenol substrate of formula 1, or of a salt thereof, and adding $I_2$ and $HIO_3$ to said aqueous solution.

8. The process according to claim 7 wherein said aqueous solution of 3,5-di-substituted phenol substrate is a crude solution deriving from an industrial process and comprising the 3,5-di-substituted phenol substrate as salt.

9. The process of claim 7 comprising adding solid $I_2$ to said aqueous solution of 3,5-di-substituted phenol substrate heated to a temperature comprised from 20 to 70° C. and then adding iodic acid.

10. The process of claim 9 wherein the iodic acid is added when the reaction mixture has a pH comprised from 5 to 6.

11. The process according to claim 1 wherein the reaction time is comprised from 5 to 9 hours.

12. A process for the preparation of a compounds of formula 5

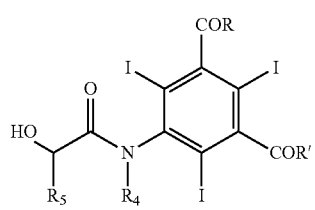

wherein:
R and R' represent, independently, a group of formula —$NHR_1$ or —$NR_2R_3$, wherein each $R_1$, $R_2$ and $R_3$ is, independently a straight or branched $C_1$-$C_6$alkyl group which is optionally substituted by one or more groups selected from hydroxyl (—OH), $C_1$-$C_5$ alkoxy and hydroxyalkoxy groups, and
$R_4$ and $R_5$ are, independently, hydrogen or a straight or branched $C_1$-$C_6$ alkyl group, optionally substituted by one or more hydroxyl or $C_1$-$C_6$ alkoxy groups, comprising:

a) preparing a triiodophenol compound of formula 2

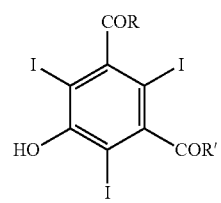

according to the process of claim 1; said process further comprising:
b) reacting said compound of formula 2, either as such or comprising the phenolic OH group in the form of a salt with an alkali metal, with a compound of formula 3

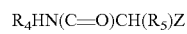

wherein $R_4$ and $R_5$ are, independently, as defined above, and Z is a halogen atom selected from chlorine or bromine, or a leaving group selected from methanesulfonyloxy, benzenesulfonyloxy, nitrobenzenesulfonyloxy, and toluensulfonyloxy, to obtain a compound of formula 4

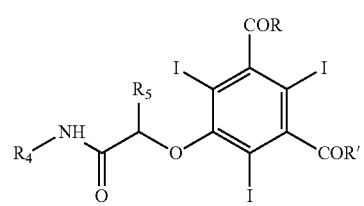

wherein R, R', $R_4$ and $R_5$ have the above reported meanings; and
c) subjecting said compound of formula 4 to Smiles's rearrangement in the presence of a base to obtain the compound of formula 5.

13. The process of claim 12 wherein both R and R' are a —$NHCH(CH_2OH)_2$ group, $R_4$ is hydrogen and $R_5$ is methyl group.

14. The process of claim 12 wherein both R and R' are a —$NHCH_2$—CH(OH)—$CH_2OH$ group, $R_4$ is methyl and $R_5$ is hydrogen.

15. The process of claim 14 comprising the steps represented in Scheme 3: